United States Patent [19]
Weichert et al.

[11] Patent Number: 6,001,881
[45] Date of Patent: Dec. 14, 1999

[54] ORTHO-SUBSTITUTED BENZOYLGUANIDINES, A PROCESS FOR THEIR PREPARATION, THEIR USE AS A MEDICAMENT OR DIAGNOSTIC AGENT, AND A MEDICAMENT COMPRISING THEM

[75] Inventors: Andreas Weichert, Egelsbach; Joachim Brendel, Bad Vilbel; Heinz-Werner Kleemann, Bischofsheim; Hans Jochen Lang, Hofheim; Jan-Robert Schwark, Frankfurt; Udo Albus, Florstadt; Wolfgang Scholz, Eschborn, all of Germany

[73] Assignee: Hoechst Aktiengesellschaft, Frankfurt am Main, Germany

[21] Appl. No.: 08/868,750

[22] Filed: Jun. 4, 1997

[30] Foreign Application Priority Data

Jun. 18, 1996 [DE] Germany ............ 196 24 178

[51] Int. Cl.⁶ ............ C07C 279/22; C07C 277/08; A61K 31/165; A61K 31/18
[52] U.S. Cl. ............ 514/620; 514/317; 514/522; 514/603; 514/618; 514/821; 514/825; 546/233; 558/413; 564/85; 564/86; 564/134; 564/139; 564/142; 564/144; 564/162; 564/164; 564/165
[58] Field of Search ............ 514/317, 522, 514/603, 618, 620, 821, 825; 546/233; 558/413; 564/85, 86, 134, 139, 142, 144, 162, 164, 165

[56] References Cited

FOREIGN PATENT DOCUMENTS

| | | |
|---|---|---|
| 9471507 | 3/1996 | Australia . |
| 9530144 | 3/1996 | Australia . |
| 2130944 | 2/1995 | Canada . |
| 2156960 | 3/1996 | Canada . |
| 0 640 588 | 1/1995 | European Pat. Off. . |
| 0 628 543 | 5/1995 | European Pat. Off. . |
| 0 699 663 | 8/1995 | European Pat. Off. . |
| 0 699 666 | 8/1995 | European Pat. Off. . |
| 0 699 660 | 3/1996 | European Pat. Off. . |
| 0 794 171 | 2/1997 | European Pat. Off. . |

*Primary Examiner*—Peter O'Sullivan
*Attorney, Agent, or Firm*—Finnegan, Henderson, Farabow, Garrett & Dunner, L.L.P.

[57] ABSTRACT

Benzoylguanidines of the formula I

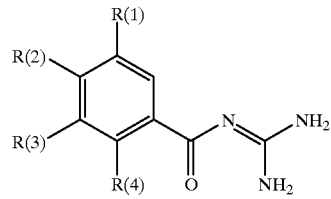

in which: R(1) to R(4) have the meanings given in the claims, are antiarrhythmic pharmaceuticals, having a cardioprotective component, which are also valuable for the prevention of ischemically induced damage, in particular in association with the triggering of ischemically induced cardiac arrhythmias. As a consequence of inhibiting the cellular Na⁺/H⁺ exchange mechanism, they are used for treating acute or chronic damage triggered by ischemia. In addition to this, they are notable for their strong inhibitory effect on the proliferation of cells. They are suitable for preventing the genesis of high blood pressure.

28 Claims, No Drawings

ORTHO-SUBSTITUTED BENZOYLGUANIDINES, A PROCESS FOR THEIR PREPARATION, THEIR USE AS A MEDICAMENT OR DIAGNOSTIC AGENT, AND A MEDICAMENT COMPRISING THEM

The invention relates to benzoylguanidines of the formula I

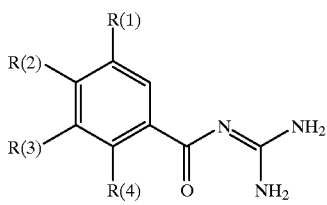

in which:
R(1) is R(13)—$SO_m$ or R(14)R(15)N—$SO_2$—;
  m is 1 or 2;
  R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(16),
  n is zero, 1, 2, 3 or 4;
  R(16) is cycloalkyl having 3, 4, 5, 6, 7 or 8 carbon atoms, phenyl, biphenylyl or naphthyl,
    where phenyl, biphenylyl and naphthyl are not substituted or are substituted by 1–3 substituents selected from the group consisting of F, Cl, $CF_3$, methyl, methoxy and NR(25)R(26);
      R(25) and R(26) are, independently of each other, hydrogen, alkyl having 1, 2, 3 or 4 carbon atoms or perfluoroalkyl having 1, 2, 3 or 4 carbon atoms;
  R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(27),
  n is zero, 1, 2, 3 or 4;
  R(27) is cycloalkyl having 3, 4, 5, 6, 7 or 8 carbon atoms, phenyl, biphenylyl or naphthyl,
    where phenyl, biphenylyl and naphthyl are not substituted or are substituted by 1–3 substituents selected from the group consisting of F, Cl, $CF_3$, methyl, methoxy and NR(28)R(29);
      R(28) and R(29) are, independently of each other, hydrogen, alkyl having 1, 2, 3 or 4 carbon atoms or perfluoroalkyl having 1, 2, 3 or 4 carbon atoms;
  R(15) is hydrogen, alkyl having 1, 2, 3 or 4 carbon atoms or perfluoroalkyl having 1, 2, 3 or 4 carbon atoms; or
  R(14) and R(15) are, together, 4 or 5 methylene groups of which one $CH_2$ group can be replaced with oxygen, S, NH, N—$CH_3$ or N-benzyl;
one of the substituents R(2) and R(3) is hydrogen;
and the other of the substituents R(2) and R(3) in each case is —CHR(30)R(31);
  R(30) is —$(CH_2)_g$—$(CHOH)_h$—$(CH_2)_i$—$(CHOH)_k$—R(32) or —$(CH_2)_g$—O—$(CH_2$—$CH_2O)_h$—R(24);
  R(24) and R(32) are, independently of each other, hydrogen or methyl;
  g, h and i are, identically or differently, zero, 1, 2, 3 or 4;
  k is 1, 2, 3 or 4;

or the other of the substituents R(2) and R(3) in each case is —C(OH)R(33)R(34);
  R(31), R(33) and R(34) are, identically or differently, hydrogen or alkyl having 1, 2, 3 or 4 carbon atoms, or
  R(33) and R(34) are, together, cycloalkyl having 3, 4, 5 or 6 carbon atoms; or
  R(33) is —$CH_2OH$;
R(4) is alkyl having 1, 2, 3 or 4 carbon atoms, alkoxy having 1, 2, 3 or 4 carbon atoms, F, Cl, Br, I, CN or —$(CH_2)_n$—$(CF_2)_o$—$CF_3$;
n is zero or 1;
o is zero, 1 or 2;
and the pharmaceutically tolerated salts thereof.

Preference is given to compounds of the formula I in which:
R(1) is R(13)—$SO_2$ or R(14)R(15)N—$SO_2$—;
  R(13) is alkyl having 1, 2, 3 or 4 carbon atoms, perfluoroalkyl having 1, 2, 3 or 4 carbon atoms, alkenyl having 3 or 4 carbon atoms or —$C_nH_{2n}$—R(16),
  n is zero, 1, 2, 3 or 4;
  R(16) is cycloalkyl having 3, 4, 5 or 6 carbon atoms, phenyl, biphenylyl or naphthyl,
    where phenyl, biphenylyl and naphthyl are not substituted or are substituted by 1–3 substituents selected from the group consisting of F, Cl, $CF_3$, methyl or methoxy;
  R(14) is hydrogen, alkyl having 1, 2, 3 or 4 carbon atoms, perfluoroalkyl having 1, 2, 3 or 4 carbon atoms, alkenyl having 3 or 4 carbon atoms or —$C_nH_{2n}$—R(27),
  n is zero, 1, 2, 3 or 4;
  R(27) is cycloalkyl having 3, 4, 5, 6, 7 or 8 carbon atoms, phenyl, biphenylyl or naphthyl,
    where phenyl, biphenylyl and naphthyl are not substituted or are substituted by 1–3 substituents selected from the group consisting of F, Cl, $CF_3$, methyl or methoxy;
  R(15) is hydrogen, alkyl having 1, 2, 3 or 4 carbon atoms or perfluoroalkyl having 1, 2, 3 or 4 carbon atoms; or
  R(14) and R(15) are, together, 4 or 5 methylene groups of which one $CH_2$ group can be replaced with oxygen, S, NH, N—$CH_3$ or N-benzyl;
one of the substituents R(2) and R(3) is hydrogen;
and the other of the substituents R(2) and R(3) in each case is —CHR(30)R(31);
  R(30) is —$(CH_2)_g$—$(CHOH)_h$—$(CH_2)_i$—$(CHOH)_k$—R(32) or —$(CH_2)_g$—O—$(CH_2$—$CH_2O)_h$—R(24);
  R(24) and R(32) are, independently of each other, hydrogen or methyl;
  g, h and i are, identically or differently, zero, 1 or 2;
  k is 1 or 2; or
the other of the substituents R(2) and R(3) in each case is —C(OH)R(33)R(34);
  R(33) and R(34) are, identically or differently, hydrogen or alkyl having 1, 2, 3 or 4 carbon atoms, or
  R(33) and R(34) are, together, cycloalkyl having 3, 4, 5 or 6 carbon atoms; or
  R(33) is —$CH_2OH$;
R(4) is alkyl having 1, 2, 3 or 4 carbon atoms, alkoxy having 1, 2, 3 or 4 carbon atoms, F, Cl, CN or $(CF_2)_o$—$CF_3$;
o is zero, 1 or 2;
and the pharmaceutically tolerated salts thereof.

Very particular preference is given to compounds of the formula I in which:
R(1) is R(13)—$SO_2$;
  R(13) is alkyl having 1, 2, 3 or 4 carbon atoms;

one of the substituents R(2) and R(3) is hydrogen;
and the other of the substituents R(2) and R(3) in each case is —C(OH)(CH$_3$)—CH$_2$OH,—CH(CH$_3$)—CH$_2$OH or C(OH)(CH$_3$)$_2$;
R(4) is alkyl having 1, 2, 3 or 4 carbon atoms, alkoxy having 1, 2, 3 or 4 carbon atoms, F, Cl, CN or —CF$_3$;
and the pharmaceutically tolerated salts thereof.

Heteroaryl having 1, 2, 3, 4, 5, 6, 7, 8 or 9 carbon atoms is understood as being radicals which are derived from phenyl or naphthyl and in which one or more CH groups are replaced with N and/or in which at least two adjacent CH groups are replaced (with the formation of a five-membered aromatic ring) with S, NH or O. Furthermore, one or both atoms of the condensation site of bicyclic radicals can also be N atoms (as in indolizinyl). Furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl are regarded, in particular, as being heteroaryl having 1, 2, 3, 4, 5, 6, 7, 8 or 9 carbon atoms.

If one of the substituents R(1) to R(4) contains one or more centers of asymmetry, these can be either in the S or the R configuration. The compounds can exist as optical isomers, as diastereomers, as racemates or as mixtures thereof.

The designated alkyl radicals can be either straight-chain or branched.

The invention also relates to a process for preparing a compound of the formula I, which comprises reacting a compound of the formula II

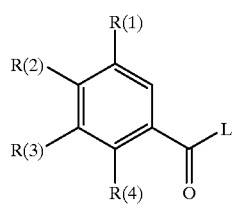

in which R(1) to R(4) have the given meaning and L is a leaving group which can readily be substituted nucleophilically, with guanidine.

The activated acid derivatives of the formula II, in which L is an alkoxy group, preferably a methoxy group, a phenoxy group, a phenylthio group, a methylthio group, a 2-pyridylthio group or a nitrogen heterocycle, preferably 1-imidazolyl, are advantageously obtained, in a manner known per se, from the underlying carbonyl chlorides (formula II, L=Cl), which, for their part, can in turn be prepared, in a manner known per se, from the underlying carboxylic acids (formula II, L=OH), for example using thionyl chloride.

In addition to the carbonyl chlorides of the formula II(L=Cl), further activated acid derivatives of the formula II can also be prepared directly, in a manner known per se, from the underlying benzoic acid derivatives (formula II, L=OH), such as the methyl esters of the formula II, in which L=OCH$_3$, by treating with gaseous HCl in methanol, the imidazolides of the formula II [L=1-imidazolyl, Staab, Angew. Chem. Int. Ed. Engl. 1, 351–367 (1962)] by treating with carbonyl diimidazole, and the mixed anhydrides II using Cl—COOC$_2$H$_5$ or tosyl chloride in the presence of triethylamine in an inert solvent, and also the activations of benzoic acids can be carried out with dicyclohexylcarbodiimide (DCC) or with O-[(cyano(ethoxycarbonyl)methylene)amino]-1, 1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A number of suitable methods for preparing activated carboxylic acid derivatives of the formula II are given, with citation of the source literature, on p. 350 of J. March, Advanced Organic Chemistry, Third Edition (John Wiley & Sons, 1985).

The reaction of an activated carboxylic acid derivative of the formula II with guanidine is effected, in a manner known per se, in a protic or aprotic polar but inert organic solvent. In this context, methanol, isopropanol or THF, at from 20° C. up to the boiling temperature of these solvents, have proved to be of value when reacting the methyl benzoates (II, L=OMe) with guanidine. Most of the reactions of compounds II with salt-free guanidine were advantageously carried out in aprotic inert solvents such as THF, dimethoxyethane or dioxane. However, water can also be used as solvent in the reaction of II with guanidine when a base such as NaOH is employed.

When L=Cl, the reaction is advantageously carried out in the added presence of an acid-capturing agent, for example in the form of excess guanidine, for the purpose of removing the hydrohalic acid.

Some of the underlying benzoic acid derivatives of the formula II are known and described in the literature. The unknown compounds of the formula II can be prepared using methods which are known from the literature. The resulting benzoic acids are converted into compounds I according to the invention using one of the above-described process variants.

Some substituents are introduced into the 2, 3, 4 and 5 positions using methods, which are known from the literature, for the palladium-mediated cross-coupling of aryl halides or aryl triflates with, for example, organostannanes, organoboronic acids or organoboranes or organocopper or organozinc compounds.

In general, benzoylguanidines I are weak bases and can bind acid with the formation of salts. Suitable acid addition salts are salts of all the pharmacologically tolerated acids, for example halides, in particular hydrochlorides, lactates, sulfates, citrates, tartrates, acetates, phosphates, methylsulfonates and p-toluene sulfonates.

The compounds I are substituted acylguanidines.

While EP-A 640 588 A1 disclosed benzoylguanidines which are of a similar structure, these benzoylguanidines do not exhibit any alkylsulfonyl or alkylsulfamoyl group, which the compounds according to the invention always possess.

While EP-A 699 660 also relates to ortho-substituted benzoylguanidines, these benzoylguanidines do not exhibit the hydroxyl group according to the invention in the R(2) or R(3) substituent.

While the prior German application 196 08 162.9 (HOE 96/F 042) also proposes ortho-substituted benzoylguanidines, none of these benzoylguanidines contains an alkylsulfonyl group.

As compared with the known compounds, the compounds according to the invention are notable for high activity in inhibiting Na$^+$/H$^+$ exchange, combined with very good water solubility.

Like the known compounds, they do not have any undesirable and disadvantageous salidiuretic properties but have very good antiarrhythmic properties as are important, for example, for treating disorders which occur in association with symptoms of oxygen lack. As a consequence of their pharmacological properties, the compounds are outstandingly suitable, as antiarrhythmic pharmaceuticals having a cardioprotective component, for infarction prophylaxis and infarction treatment and for treating angina pectoris, in association with which they also inhibit or strongly diminish, in a preventive manner, the pathophysiological processes associated with the development of ischemically induced damage, in particular in association with the triggering of ischemically induced cardiac arrhythmias. On account of their protecting effects against pathological hypoxic and ischemic situations, the novel compounds of the formula I can, as a consequence of inhibiting the cellular $Na^+/H^+$ exchange mechanism, be used as pharmaceuticals for treating all acute or chronic damage which is triggered by ischemia or disorders which are primarily or secondarily induced thereby. This relates to their use as pharmaceuticals for surgical interventions, for example in association with organ transplantations, where the compounds can be used both for protecting the organs in the donor, before and during removal, for protecting removed organs, for example when treating them with, or storing them in, physiological bathing fluids, and also when transferring the organs into the recipient organism. The compounds are likewise valuable, protective pharmaceuticals when carrying out angioplastic surgical interventions, for example on the heart and on peripheral blood vessels. In conformity with their protective effect against ischemically induced damage, the compounds are also suitable as pharmaceuticals for treating ischemias of the nervous system, in particular of the CNS, where they are suitable, for example, for treating stroke or cerebral edema. In addition to this, the novel compounds of the formula I are likewise suitable for treating forms of shock, for example allergic, cardiogenic, hypovolemic and bacterial shock.

Over and above this, the novel compounds of the formula I are notable for their strong inhibitory effect on the proliferation of cells, for example on fibroblast cell proliferation and the proliferation of the smooth muscle cells of the blood vessels. For this reason, the compounds of the formula I are suitable as valuable therapeutic agents for disorders in which cell proliferation constitutes a primary or secondary cause and can therefore be used as antiatherosclerotic agents, and as agents against diabetic late complications, cancerous diseases, fibrotic diseases such as pulmonary fibrosis, hepatic fibrosis or renal fibrosis, and organ hypertrophies and hyperplas as, in particular in hyperplasia or hypertrophy of the prostate.

The novel compounds are effective inhibitors of the cellular sodium/proton antiporter ($Na^+/H^+$ exchanger), which, in many disorders (essential hypertension, atherosclerosis, diabetes, etc.), is also elevated in those cells, such as erythrocytes, thrombocytes or leukocytes, which are readily accessible to measurement. The novel compounds are therefore suitable as outstanding and simple scientific tools, for example in their use as diagnostic agents for determining and differentiating particular forms of hypertension and also atherosclerosis, diabetes, proliferative disorders, etc. Over and above this, the compounds of the formula I are suitable for preventive therapy for preventing the genesis of high blood pressure, for example of essential hypertension.

It has also been found that compounds of the formula I exhibit a favorable influence on serum lipoproteins. It is generally recognized that blood fat values which are too high, so-called hyperlipoproteinemias, constitute an important risk factor for the genesis of atherosclerotic changes in the blood vessels, in particular coronary heart disease. Exceptional significance for the prophylaxis and regression of atherosclerotic changes is therefore attached to the lowering of elevated serum lipoproteins. In addition to reducing total serum cholesterol, particular importance is attached to lowering the proportion of specific atherogenic lipid fractions, in particular the low density lipoproteins (LDL) and the very low density lipoproteins (VLDL), in this total cholesterol, since these lipid fractions constitute an atherogenic risk factor. By contrast, a protective function against coronary heart disease is ascribed to the high density lipoproteins. Accordingly, hypolipidemic agents should be able to lower the VLDL and LDL serum cholesterol fractions, in particular, in addition to lowering total cholesterol. It has now been found that compounds of the formula I exhibit valuable, therapeutically utilizable properties with regard to exerting an influence on serum lipid levels. Thus, they significantly lower elevated serum concentrations of LDL and VLDL as can be observed, for example, as the result of an elevated dietary intake of a cholesterol- and lipid-rich diet or in association with pathological changes in metabolism, for example genetically determined hyperlipidemias. For this reason, they can be enlisted for the prophylaxis and regression of atherosclerotic changes since they eliminate a causal risk factor. These hyperlipidemias include not only the primary hyperlipidemias but also certain secondary hyperlipidemias, as occur, for example, in association with diabetes. In addition to this, the compounds of the formula I lead to a marked reduction in the infarctions which are induced by metabolic anomalies and lead, in particular, to a significant diminution in the size and severity of the induced infarction. Furthermore, compounds of the formula I lead to an effective protection against damage due to endothelial damage which is induced by metabolic anomalies. As a result of this ability to protect the blood vessels against the syndrome of endothelial dysfunction, compounds of the formula I are valuable pharmaceuticals for preventing and treating coronary vessel spasms, atherogenesis and atherosclerosis, left-ventricular hypertrophy and dilated cardiomyopathy, and thrombotic disorders.

The said compounds are therefore advantageously used for preparing a medicament for treating hypercholesterolemia, for preparing a medicament for preventing atherogenesis, for preparing a medicament for preventing and treating atherosclerosis, for preparing a medicament for preventing and treating disorders which are triggered by elevated cholesterol levels, for preparing a medicament for preventing and treating disorders which are triggered by endothelial dysfunction, for preparing a medicament for preventing and treating atherosclerosis-induced hypertension, for preparing a medicament for preventing and treating atherosclerosis-induced thrombosis, for preparing a medicament for preventing and treating ischemic damage and post-ischemic reperfusion damage which are induced by hypercholesterolemia and endothelial dysfunction, for preparing a medicament for preventing and treating cardiac hypertrophies and cardiomyopathies which are induced by hypercholesterolemia and endothelial dysfunction, for preparing a medicament for preventing and treating coronary vessel spasms and myocardial infarctions which are induced by hypercholesterolemia and endothelial dysfunction, for preparing a medicament for treating said ailments in combinations with hypotensive compounds, preferably with angiotensin converting enzyme (ACE) inhibitors and angiotensin receptor antagonist. A combination of an NHE inhibitor of the formula I with a blood fat level-lowering active compound, preferably with an HMG-CoA reductase inhibitor (for example lovastatin or pravastatin), with the latter bringing about a hypolipidemic effect and thereby intensifying the hypolipidemic properties of the NHE inhibitor of the formula I, is found to be an advantageous combination which has an augmented effect and which involves decreased use of active compound.

The administration of sodium/proton exchange inhibitors of the formula I, as novel pharmaceuticals for lowering elevated blood fat levels, and the combination of sodium/proton exchange inhibitors with hypotensive pharmaceuticals and/or pharmaceuticals having a hypolipidemic effect are claimed.

In this context, pharmaceuticals which comprise a compound I can be administered orally, parenterally, intravenously, rectally or by inhalation, with the preferred route of administration depending on the particular symptoms of the disease. In this context, the compounds I can be used alone or together with pharmaceutical auxiliary substances, and be used both in veterinary medicine and human medicine.

Based on his specialist knowledge, the skilled person is familiar with the auxiliary substances which are suitable for the desired pharmaceutical formulation. Antioxidants, dispersing agents, emulsifiers, defoaming agents, taste corrigents, preservatives, solubilizers or dyes can, for example, be used in addition to solvents, gel-forming agents, suppository bases, tablet auxiliary substances and other active compound excipients.

For a form for oral use, the active compounds are mixed with the additives, such as carrier substances, stabilizers or inert diluents, which are suitable for the purpose and brought, using the customary methods, into the suitable forms for administration, such as tablets, coated tablets, hard gelatin capsules and aqueous, alcoholic or oily solutions. Gum arabic, magnesium hydroxide, magnesium carbonate, potassium phosphate, lactose, glucose or starch, in particular corn starch, can, for example, be used as inert excipients. In this context, the preparation can be effected either as a dry granulate or as a wet granulate. Examples of suitable oily carrier substances or solvents are vegetable or animal oils, such as sunflower oil or cod liver oil.

For subcutaneous or intravenous administration, the active compounds are brought, if desired together with the substances, such as solubilizers, emulsifiers or other auxiliary substances, which are customary for the purpose, into solution, suspension or emulsion. Examples of suitable solvents are: water, physiological sodium chloride solution or alcohols, for example ethanol, propanol or glycerol, and, in addition, sugar solutions, such as glucose or mannitol solutions, or else a mixture of the different solvents mentioned.

Examples of suitable pharmaceutical formulations for administration in the form of aerosols or sprays are solutions, suspensions or emulsions of the active compound of the formula I in a pharmaceutically harmless solvent, such as, in particular, ethanol or water, or a mixture of these solvents.

The formulation can, as required, also comprise other pharmaceutical auxiliary substances such as surfactants, emulsifiers and stabilizers and also a propellant gas. Such a preparation customarily comprises the active compound at a concentration of from about 0.1 to 10, in particular of from about 0.3 to 3,% by weight.

The dose of the active compound of the formula I to be administered, and the frequency of administration, depend on the strength and duration of the action of the compounds used; they also depend on the nature and severity of the disorder to be treated and on the sex, age, weight and individual responsiveness of the mammalian subject to be treated.

On average, the daily dose of a compound of the formula I in the case of a patient of approximately 75 kg in weight is at least 0.001 mg/kg, preferably 0.01 mg/kg, to at most 10 mg/kg, preferably 1 mg/kg, of body weight. In the case of acute outbreaks of the disorder, for example immediately after the patient has suffered a cardiac infarction, even higher and, in particular more frequent, doses may also be necessary, for example up to 4 individual doses per day. Up to 200 mg per day may be necessary in the case of i.v. use, in particular, for example in the case of an infarction patient in intensive care.

As used herein, the term "therapeutically effective amount" means an amount of the compound which is effective in treating the named disorder. A therapeutically effective amount can be readily determined by the attending diagnostician, as one skilled in the art, by the use of known techniques and by observing results obtained under analogous circumstances.

As used herein, the term "patient" refers to a mammal such as a dog, cat, guinea pig, mouse, rat or human being.

The terms "treating" or "to treat" means to alleviate symptoms, eliminate the causation either on a temporary or permanent basis, or to prevent or slow the appearance of symptoms of the named disorder.

The disclosure of German patent application ser. no. 19624178.2 filed Jun. 18, 1996 is herein incorporated by reference.

List of abbreviations:

MeOH methanol

DMF N,N-dimethylformamide

RT room temperature

EA ethyl acetate (EtOAc)

m.p. melting point

THF tetrahydrofuran eq. equivalent

Experimental Section

General protocol for preparing benzoylguanidines (I)

Variant A: from benzoic acids (II, L=OH)

1.0 eq. of the benzoic acid derivative of the formula II is dissolved or suspended in anhydrous THF (5 ml/mmol), and 1.1 eq. of carbonyldiimidazole are then added. After stirring at RT for 2 hours, 5.0 eq. of guanidine are introduced into the reaction solution. After stirring overnight, the THF is distilled off under reduced pressure (rotary evaporator), water is added, the pH is adjusted to from 6 to 7 with 2 N HCl and the corresponding benzoylguanidine (formula I) is filtered off. The benzoylguanidines which are obtained in this way can be converted into the corresponding salts by treatment with aqueous, methanolic or ethereal hydrochloric acid or other pharmacologically tolerated acids.

General protocol for preparing benzoylguanidines (I)

Variant B: from alkyl benzoates (II, L=O-alkyl)

1.0 eq. of the alkyl benzoate of the formula II and 5.0 eq. of guanidine (free base) are dissolved in isopropanol or suspended in THF and heated to boiling until reaction is complete (monitoring by thin layer chromatography) (typical reaction time: from 2 to 5 h). The solvent is distilled off under reduced pressure (rotary evaporator) and the residue is taken up in EA and this solution is washed 3× with NaHCO$_3$ solution. The solvent solution is dried over Na$_2$SO$_4$, the solvent is distilled off in vacuo, and the residue is chromatographed on silica gel using a suitable mobile phase, for example EA/MeOH 5:1.

(Salt formation: compare Variant A)

EXAMPLE 1

2-Chloro-3-(1'-hydroxy-2'-propyl)-5-methylsulfonylbenzoylguanidine Colorless crystals, m.p. 211° C.(decomp.).

Synthesis route:

a) Methyl 2-chloro-3-iodo-5-methylsulfonylbenzoate from methyl 2-chloro-5-methylsulfonylbenzoate by means of Olah iodination with 1 eq. of N-iodosuccinimide in 5 eq. of trifluoromethanesulfonic acid at RT for 24 h, colorless crystals, m.p. 155–58° C.

b) Methyl 2-chloro-3-isopropenyl-5-methylsulfonylbenzoate from methyl 2-chloro-3-iodo-5-methylsulfonylbenzoate by means of cross-coupling with 1.5 equivalents of isopropenylzinc chloride in THF under reflux in the presence of catalytic quantities of palladium(II) acetate and copper(I) iodide, aqueous working-up, extraction with ethyl acetate and subsequent column chromatography on silica gel using ethyl acetate/n-heptane (3:7). Colorless oil, MS: $M^++H=289$.

c) 2-Chloro-3-[1'-hydroxy-2'-propyl]-5-methylsulfonylbenzoic acid by the hydroboration of methyl 2-chloro-3-isopropenyl-5-methylsulfonyl benzoate with borane/THF complex in THF under reflux for 3 h, colorless crystals, m.p. 175–77° C.

d) Methyl 2-chloro-3-[1'-hydroxy-2'-propyl]-5-methylsulfonylbenzoate from c) by esterification with 3 eq. of methyl iodide in the presence of potassium carbonate in DMF at RT for 3 h, aqueous working-up, yellowish oil, $M^++H=307$.

e) 2-Chloro-3-[1'-hydroxy-2'-propyl]-5-methylsulfonylbenzoylguanidine from d) in accordance with the general protocol, Variant B.

EXAMPLE 2

2-Methoxy-3-(1'-hydroxy-2'-propyl)-5-methylsulfonylbenzoyl-guanidine colorless crystals, m.p. 179–80° C.(decomp.).

Synthesis route:

a) 2-Methoxy-5-methylsulfonylbenzoic acid from methyl 2-chloro-5-methylsulfonylbenzoate using 10 eq. of sodium methoxide in the presence of copper(II) chloride in methanol under reflux for 4 h, yellowish solid, m.p. 190–92° C.

b) 2-Methoxy-3-iodo-5-methylsulfonylbenzoic acid from 2-methoxy-5-methylsulfonylbenzoic acid by means of Olah iodination using 1 eq. of N-iodo-succinimide in 5 eq. of trifluoromethanesulfonic acid at RT for 24 h, colorless crystals, m.p. 205–07° C.

c) Methyl 2-methoxy-3-iodo-5-methylsulfonylbenzoate from b) by esterification with an excess of hydrogen chloride in methanol at RT for 24 h, aqueous working-up, colorless solid, m.p. 140° C.

d) Methyl 2-methoxy-3-isopropenyl-5-methylsulfonylbenzoate from methyl 2-methoxy-3-iodo-5-methylsulfonylbenzoate in analogy with method 1 b), colorless oil, $M^++H=285$.

e) 2-Methoxy-3-[1'-hydroxy-2'-propyl]-5-methylsulfonylbenzoic acid from d) in analogy with method 1 c), colorless solid, amorphous, $M^++H=289$.

f) Methyl 2-methoxy-3-[1'-hydroxy-2'-propyl]-5-methylsulfonyl-benzoate by esterification with 3 eq. of methyl iodide in the presence of potassium carbonate in DMF at RT for 3 h, aqueous working-up, pale yellow oil, $M^++H=303$.

g) 2-Methoxy-3-[1'-hydroxy-2'-propyl]-5-methylsulfonylbenzoyl-guanidine from 2 f) in accordance with the general protocol, Variant B.

EXAMPLE 3

2-Methyl-3-(1'-hydroxy-2'-propyl)-5-methylsulfonylbenzoyl-guanidine Colorless crystals, m.p. 208–09° C.(decomp.).

Synthesis route:

a) Methyl 2-methyl-5-methylsulfonylbenzoate from methyl 2-chloro-5-methylsulfonylbenzoate by means of cross-coupling with 2 eq. of methylzinc chloride in THF/DMF under reflux in the presence of catalytic quantities of palladium(II) acetate, triphenylphosphine and copper(I) iodide, aqueous working-up, extraction with ethyl acetate and subsequent column chromatography on silica gel using ethyl acetate/n-heptane (3:7), colorless crystals, m.p. 95–96° C.

b) Methyl 2-methyl-3-iodo-5-methylsulfonylbenzoate from methyl 2-methyl-5-methylsulfonylbenzoate by means of Olah iodination using 1 eq. of N-iodosuccinimide in 5 eq. of trifluoromethanesulfonic acid at RT for 24 h, colorless crystals, m.p. 137–38° C.

c) Methyl 2-methyl-3-isopropenyl-5-methylsulfonylbenzoate from methyl 2-methyl-3-iodo-5-methylsulfonylbenzoate by means of cross-coupling with 1.5 equivalents of isopropenylzinc chloride in THF under reflux in the presence of catalytic quantities of palladium(II) acetate, triphenylphosphine and copper(I) iodide, aqueous working-up, extraction with ethyl acetate and subsequent column chromatography on silica gel using ethyl acetate/n-heptane (3:7), colorless oil, $M^++H=269$.

d) 2-Methyl-3-[1'hydroxy-2'propyl]-5-methylsulfonylbenzoic acid by means of the hydroboration of methyl 2-methyl-3-isopropenyl-5-methylsulfonylbenzoate with borane/THF complex in THF under reflux for 3 h, amorphous solid, $M^++H=273$.

e) Methyl 2-methyl-3-[1'-hydroxy-2'-propyl]-5-methylsulfonylbenzoate by means of esterification with 3 eq. of methyl iodide in the presence of potassium carbonate in DMF at RT for 3 h, aqueous working-up, pale yellow oil, $M^++H=287$.

f) 2-Methyl-3-[1'-hydroxy-2'-propyl]-5-methylsulfonylbenzoylguanidine from e) in accordance with the general protocol, Variant B.

Pharmacological data:

Inhibition of the $Na^+/H^+$ exchanger of rabbit erythrocytes

New Zealand White rabbits (Ivanovas) were given a standard diet containing 2% cholesterol for six weeks in order to activate the $Na^+/H^+$ exchange and thereby make it possible to use flame photometry to determine the influx of $Na^+$ into the erythrocytes via $Na^+/H^+$ exchange. Blood was withdrawn from the aural arteries and rendered incoagulable using 25 IU of potassium heparin. Part of each sample was used for determining the hematocrit in duplicate by means of centrifugation. Aliquots of in each case 100 $\mu l$ were used to measure the initial content of $Na^+$ in the erythrocytes.

In order to determine the amiloride-sensitive sodium influx, 100 $\mu l$ of each blood sample were in each case incubated, at 37° C. and pH 7.4, in 5 ml of a hyperosmolar salt/sucrose medium (mmol/l: 140 NaCl, 3 KCl, 150 sucrose, 0.1 ouabain, 20 tris(hydroxymethyl) aminomethane). After that, the erythrocytes were washed three times with ice-cold $MgCl_2$/ouabain solution (mmol/l: 112 $MgCl_2$, 0.1 ouabain) and hemolyzed in 2.0 ml of distilled water. The intracellular sodium content was determined by means of flame photometry.

The net $Na^+$ influx was calculated from the difference between the initial sodium values and the sodium content of the erythrocytes after incubation. The amiloride-inhibitable sodium influx was obtained from the difference in the sodium content of the erythrocytes after incubating with and without $3\times10^4$ mol of amiloride/l. The same procedure was adopted in the case of the novel compounds as well.

Results
Inhibition of the $Na^+/H^+$ exchanger:
The compounds of all the examples have $IC_{50}$ values of less than 10 μmolar.

What is claimed is:
1. A benzoylguanidine compound of the formula I

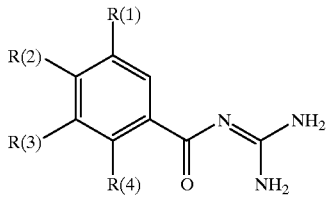

wherein
R(1) is R(13)—$SO_m$ or R(14)R(15)N—$SO_2$—;
   m is 1 or 2;
   R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(16),
   n is zero, 1, 2, 3 or 4;
   R(16) is cycloalkyl having 3, 4, 5, 6, 7 or 8 carbon atoms, phenyl, biphenylyl or naphthyl,
      where phenyl, biphenylyl and naphthyl are not substituted or are substituted by 1–3 substituents selected from the group consisting of F, Cl, $CF_3$, methyl, methoxy and NR(25)R(26);
      R(25) and R(26) are, independently of each other, hydrogen, alkyl having 1, 2, 3 or 4 carbon atoms or perfluoroalkyl having 1, 2, 3 or 4 carbon atoms;
   R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(27),
   n is zero, 1, 2, 3 or 4;
   R(27) is cycloalkyl having 3, 4, 5, 6, 7 or 8 carbon atoms, phenyl, biphenylyl or naphthyl,
      where phenyl, biphenylyl and naphthyl are not substituted or are substituted by 1–3 substituents selected from the group consisting of F, Cl, $CF_3$, methyl, methoxy and NR(28)R(29);
      R(28) and R(29) are, independently of each other, hydrogen, alkyl having 1, 2, 3 or 4 carbon atoms or perfluoroalkyl having 1, 2, 3 or 4 carbon atoms;
   R(15) is hydrogen, alkyl having 1, 2, 3 or 4 carbon atoms or perfluoroalkyl having 1, 2, 3 or 4 carbon atoms; or
   R(14) and R(15) are, together, 4 or 5 methylene groups of which one $CH_2$ group can be replaced with oxygen, S, NH, N—$CH_3$ or N-benzyl;
one of the substituents R(2) and R(3) is hydrogen;
and the other of the substituents R(2) and R(3) in each case is —CHR(30)R(31);
   R(30) is —$(CH_2)_g$—$(CHOH)_h$—$(CH_2)_i$—$(CHOH)_k$—R(32) or —$(CH_2)_g$—O—$(CH_2$—$CH_2O)_h$—R(24);
   R(24) and R(32) are, independently of each other, hydrogen or methyl;
   g, h and i are, identically or differently, zero, 1, 2, 3 or 4;
   k is 1,2,3 or 4;
or the other of the substituents R(2) and R(3) in each case is —C(OH)R(33)R(34);
   R(31), R(33) and R(34) are, identically or differently, hydrogen or alkyl having 1, 2, 3 or 4 carbon atoms, or
   R(33) and R(34) are, together, cycloalkyl having 3, 4, 5 or 6 carbon atoms; or
   R(33) is —$CH_2OH$;
R(4) is alkyl having 1, 2, 3 or 4 carbon atoms, alkoxy having 1, 2, 3 or 4 carbon atoms, F, Cl, Br, I, CN or —$(CH_2)_n$—$(CF_2)_o$—$CF_3$;
n is zero or 1;
o is zero, 1 or 2;
and the pharmaceutically tolerated salts thereof.
2. The compound of claim 1 wherein
R(1) is R(13)—$SO_2$ or R(14)R(15)N—$SO_2$—;
   R(13) is alkyl having 1, 2, 3 or 4 carbon atoms, perfluoroalkyl having 1, 2, 3 or 4 carbon atoms, alkenyl having 3 or 4 carbon atoms or —$C_nH_{2n}$—R(16),
   n is zero, 1, 2, 3 or 4;
   R(16) is cycloalkyl having 3, 4, 5 or 6 carbon atoms, phenyl, biphenylyl or naphthyl,
      where phenyl, biphenylyl and naphthyl are not substituted or are substituted by 1–3 substituents selected from the group consisting of F, Cl, $CF_3$, methyl or methoxy;
   R(14) is hydrogen, alkyl having 1, 2, 3 or 4 carbon atoms, perfluoroalkyl having 1, 2, 3 or 4 carbon atoms, alkenyl having 3 or 4 carbon atoms or —$C_nH_{2n}$—R(27),
   n is zero, 1, 2, 3 or 4;
   R(27) is cycloalkyl having 3, 4, 5, 6, 7 or 8 carbon atoms, phenyl, biphenylyl or naphthyl,
      where phenyl, biphenylyl and naphthyl are not substituted or are substituted by 1–3 substituents selected from the group consisting of F, Cl, $CF_3$, methyl or methoxy;
   R(15) is hydrogen, alkyl having 1, 2, 3 or 4 carbon atoms or perfluoroalkyl having 1, 2, 3 or 4 carbon atoms; or
   R(14) and R(15) are, together, 4 or 5 methylene groups of which one $CH_2$ group can be replaced with oxygen, S, NH, N—$CH_3$ or N-benzyl;
one of the substituents R(2) and R(3) is hydrogen;
and the other of the substituents R(2) and R(3) in each case is —CHR(30)R(31);
   R(30) is —$(CH_2)_g$—$(CHOH)_h$—$(CH_2)_i$—$(CHOH)_k$—R(32) or —$(CH_2)_g$—O—$(CH_2$—$CH_2O)_h$—R(24);
   R(24) and R(32) are, independently of each other, hydrogen or methyl;
   g, h and i are, identically or differently, zero, 1 or 2;
   k is 1 or 2;
or the other of the substituents R(2) and R(3) in each case is —C(OH)R(33)R(34);
   R(33) and R(34) are, identically or differently, hydrogen or alkyl having 1, 2, 3 or 4 carbon atoms, or
   R(33) and R(34) are, together, cycloalkyl having 3, 4, 5 or 6 carbon atoms; or
   R(33) is —$CH_2OH$;
R(4) is alkyl having 1, 2, 3 or 4 carbon atoms, alkoxy having 1, 2, 3 or 4 carbon atoms, F, Cl, CN or $(CF_2)_o$—$CF_3$;
o is zero, 1 or 2.
3. The compound of claim 2 wherein
R(1) is R(13)—$SO_2$;
   R(13) is alkyl having 1, 2, 3 or 4 carbon atoms;
one of the substituents R(2) and R(3) is hydrogen;
and the other of the substituents R(2) and R(3) in each case is —C(OH)($CH_3$)—$CH_2OH$, —CH($CH_3$)—$CH_2OH$ or C(OH)($CH_3$)$_2$;

R(4) is alkyl having 1, 2, 3 or 4 carbon atoms, alkoxy having 1, 2, 3 or 4 carbon atoms, F, Cl, CN or —CF$_3$.

4. A process for preparing the compound of claim 1, which comprises reacting a compound of the formula II

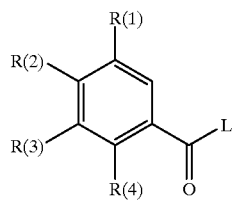

II in which R(1) to R(4) have the meaning given in claim 1 and L is a leaving group which can readily be substituted nucleophilically, with guanidine.

5. A compound according to claim 1 which is 2-chloro-3-(1'-hydroxy-2'-propyl)-5-methylsulfonylbenzoylguanidine.

6. A compound according to claim 1 which is 2-methoxy-3-(1'-hydroxy-2'-propyl)-5-methylsulfonylbenzoylguanidine.

7. A compound according to claim 1 which is 2-methyl-3-(1'-hydroxy-2'-propyl)-5-methylsulfonylbenzoylguanidine.

8. A method of treating a disorder caused by ischemic conditions in a patient comprising administering to a patient in need thereof a therapeutically effective amount of a compound of claim 1.

9. A pharmaceutical composition comprising a therapeutically effective amount of a compound of claim 1 in admixture with a physiologically acceptable carrier.

10. A method of treating cardiac infarction comprising administering to a patient in need thereof a therapeutically effective amount of a compound of claim 1.

11. A method of treating arrhythmia comprising administering to a patient in need thereof a therapeutically effective amount of a compound of claim 1.

12. A method of treating angina pectoris comprising administering to a patient in need thereof a therapeutically effective amount of a compound of claim 1.

13. A method of treating ischemic conditions of the heart comprising administering to a patient in need thereof a therapeutically effective amount of a compound of claim 1.

14. A method of treating ischemic conditions of the peripheral and central nervous system and stroke comprising administering to a patient in need thereof a therapeutically effective amount of a compound of claim 1.

15. A method of treating ischemic conditions of peripheral organs and limbs comprising administering to a patient in need thereof a therapeutically effective amount of a compound of claim 1.

16. A method of treating shock conditions in a patient comprising administering to a patient in need thereof a therapeutically effective amount of a compound of claim 1.

17. A method of preparing a patient for surgical operation or organ transplantation comprising administering to the patient in need thereof a therapeutically effective amount of a compound of claim 1.

18. The method of preserving and storing a transplant organ for surgical transplantation comprising administering to the organ a therapeutically effective amount of a compound of claim 1.

19. A method of treating a disease in which cell proliferation constitutes a primary or secondary cause comprising administering to a patient in need thereof a therapeutically effective amount of a compound of claim 1.

20. The method of claim 19 wherein the disease in which cell proliferation constitutes a primary or secondary cause is atherosclerosis.

21. The method of claim 19 wherein the disease in which cell proliferation constitutes a primary or secondary cause is diabetic late complications.

22. The method of claim 19 wherein the disease in which cell proliferation constitutes a primary or secondary cause is cancer.

23. The method of claim 19 wherein the disease in which cell proliferation constitutes a primary or secondary cause is fibrotic disease.

24. The method of claim 23 wherein the fibrotic disease is pulmonary fibrosis.

25. The method of claim 23 wherein the fibrotic disease is hepatic fibrosis.

26. The method of claim 23 wherein the fibrotic disease is renal fibrosis.

27. The method of claim 19 wherein the disease in which cell proliferation constitutes a primary or secondary cause is prostate hyperplasia.

28. A method of treating disturbances of fat metabolism comprising administering to a patient in need thereof a therapeutically effective amount of a compound of claim 1.

* * * * *